United States Patent [19]

McMahon et al.

[11] Patent Number: 5,166,078
[45] Date of Patent: Nov. 24, 1992

[54] HAPTEN-MACROMOLECULE CONJUGATES USEFUL IN HAPTEN ASSAYS

[75] Inventors: Philip L. McMahon, Falmouth; Susan Faust, Bar Mills, both of Me.

[73] Assignee: Idexx Laboratories, Inc., Westbrook, Me.

[21] Appl. No.: 897,984

[22] Filed: Aug. 19, 1986

[51] Int. Cl.$^5$ .................................... G01N 33/531
[52] U.S. Cl. .................................... 436/543; 436/8; 436/822; 436/547; 436/548; 436/815; 436/518; 435/967; 435/7.31
[58] Field of Search .................. 435/7.31, 967, 975; 436/543, 518, 547, 548, 815, 822; 424/88

[56] References Cited

U.S. PATENT DOCUMENTS

| | | | |
|---|---|---|---|
| 3,322,632 | 5/1967 | Schwick et al. | 167/78 |
| 3,514,429 | 5/1970 | Stahmann et al. | 260/80.73 |
| 4,036,823 | 7/1977 | Soares | 260/112 R |
| 4,347,312 | 8/1982 | Brown et al. | 435/7.93 |
| 4,410,634 | 10/1983 | Cooper et al. | 436/500 |
| 4,530,786 | 7/1985 | Dunbar et al. | 436/547 |
| 4,772,551 | 9/1988 | Hart et al. | 435/28 |

FOREIGN PATENT DOCUMENTS

| | | | |
|---|---|---|---|
| 0007163 | 1/1980 | European Pat. Off. | 436/519 |
| 0144154 | 6/1985 | European Pat. Off. | |
| 0002554 | 1/1981 | Japan | 435/7 |
| 1100660 | 5/1986 | Japan | 435/7 |
| 8204323 | 12/1982 | World Int. Prop. O. | 435/7 |
| 8603841 | 7/1986 | World Int. Prop. O. | |

OTHER PUBLICATIONS

Voller "Heterogeneous Enzyme-Immunoassays and Their Applications" in Enzyme-Immunoassay, Maggio, Editor, pp. 181-196 (1980).
Furuya et al. "Gas-liquid chromatographic demonstration of the specificity of rabbit IgG antibody to the pesticide DDT and its metabolites", Mol. Immund. 18: 95-102 (1981).
The Merck Index pp. 125, 409-410, 27-28, 1018-1020 (1983).
Chu et al., J. Ass. Off. Anal. Chem. vol. 60, No. 4, "Preparation and Characterization of Aflatoxin $B_1$-1-(O-carboxymethyl) Oxime" pp. 791-794, 1977.
Chu et al., Appl. and Env. Micro., vol. 33, No. 5, "Production of Antibody Against Aflatoxin $B_1$" pp. 1125-1128, 1977.
Hammond, Chemical Abstracts, vol. 104(9), No. 65415z, 1985.
Experientia, vol. 35, No. 8, Aug. 1979, Basel CH pp. 1104-1107; W. O. Harder et al.: "Production and Characterization of Antibody Against Aflatoxin M1", p. 1106.
Chemical Abstracts, vol. 100, No. 1, Jan. 2, 1984, p. 389; col. 2; Ref. No. 4464K.
Chemical Abstracts, vol. 106, No. 25, Jun. 25, 1987, p. 190; col. 2; Ref. No. 208905p.

Primary Examiner—Esther L. Kepplinger
Assistant Examiner—Carol E. Bidwell

[57] ABSTRACT

The invention is a method for measuring a hapten poorly soluble in aqueous solution in a sample which includes the steps of reacting the hapten with an antibody specific for the hapten; and comparing the result of the reaction of the hapten and the antibody with the result of the reaction of the antibody and a water-soluble conjugate of the hapten and a water-soluble macromolecule having a molecular weight greater than about 1,000.

7 Claims, No Drawings

HAPTEN-MACROMOLECULE CONJUGATES USEFUL IN HAPTEN ASSAYS

BACKGROUND OF THE INVENTION

This invention relates to measuring haptens in samples.

Generally, the control (i.e., standard) for immunoassay of a hapten is the hapten itself. A hapten is a molecule which reacts selectively in vitro with an antibody, but cannot stimulate antibody formation unless it is conjugated with a larger carrier molecule.

SUMMARY OF THE INVENTION

In general the invention features a method for measuring a hapten poorly soluble in aqueous solution in a sample. The method includes the steps of reacting the hapten with an antibody specific for the hapten, and comparing the result of the reaction between the hapten and antibody with the result of the reaction between the antibody and a water-soluble conjugate of the hapten and a water-soluble macromolecule having a molecular weight greater than about 1,000. As used herein, the term "conjugate" means a hapten and a macromolecule bonded together through covalent, coordination covalent, or secondary bonding forces, e.g., Van der Waals bonding forces.

The invention also features a kit for measuring a hapten poorly soluble in aqueous solution in a sample. The method includes an antibody specific for the hapten, and a water-soluble conjugate of the hapten and a water-soluble macromolecule having a molecular weight greater than about 1,000.

In preferred embodiments, the aqueous solubility of the hapten is less than about 0.01 g/ml; the hapten is a mycotoxin, e.g., ocratoxin, vomitoxin, or an aflatoxin, e.g., aflatoxin $B_1$; penicillin; a pesticide; e.g., DDT; and the macromolecule is a protein, preferably bovine serum albumin, ferritin, lactalbumin, human serum albumin, or polylysine.

The invention permits fast, safe, and convenient measurement of haptens which are either insoluble or unstable in aqueous solution by providing as standards conjugates which are soluble and stable in aqueous solution; the standards are used to determine the amount of the hapten present. Because the conjugates are soluble and stable in aqueous solution, it is not necessary to store the conjugates in organic solvents or in lyophilized form prior to use. Thus, the invention eliminates the necessity of handling and disposing of organic solvents, and of weighing out lyophilized hapten for the control solution each time an immunoassay is performed. Furthermore, the conjugates made with toxic haptens, e.g., aflatoxin $B_1$ or DDT, are less hazardous than organic solutions of the haptens because the conjugates, being water-soluble, penetrate the skin less readily than the organic solutions.

Other features and advantages of the invention will be apparent from the following description of the Preferred embodiments thereof and from the claims.

DESCRIPTION OF THE PREFERRED EMBODIMENTS

We now describe the structure, synthesis, and use of preferred embodiments of the invention.

Structure and Synthesis

In general, water-soluble, water-stable conjugates for use as control substances in detecting the presence of a hapten are conjugates, preferably covalent conjugates, formed between the hapten and a water-soluble macromolecule having a molecular weight greater than 1,000. The conjugates are prepared by coupling the hapten and the macromolecule using standard techniques and reagents such as hydrazides, azides, cyanogen bromide, N,N-o-phenylene dimaleimide, m-maleimidobenzoyl-N-hydroxysuccinimide ester, glutaraldehyde, carbodiimides, diisocyanates, (o-carboxymethyl) hydroxylamines, anhydrides, diazonium compounds and dihalogenated dinitrobenzenes.

The hapten may be any one or more of a wide variety of materials whose aqueous solubility is less than 0.01 g/ml, for example, drugs, animal and plant hormones, pesticides, or toxins. Suitable macromolecules for conjugating with the hapten include proteins, e.g., bovine serum albumin (BSA), human serum albumin, egg albumin, polylysine, immunoglobulin, lipid A, and collagen.

The conjugates thus prepared are water soluble because the macromolecular component of the conjugates is water-soluble. The conjugates are also stable in aqueous solution, unlike the hapten, because of the macromolecular component.

Once the conjugate has been formed it is diluted in a suitable aqueous buffer and stored at about 2°–7° C. until used as the standard in an immunoassay.

The conjugates of the invention are used as controls in any of a variety of standard immunoassays. Generally, a sample containing the hapten to be detected is contacted with an antibody having a specific affinity for the hapten; the antibody and hapten react with each other. To determine how much of the hapten is present in the sample, the reaction between the hapten in the sample and the antibody is compared with the reaction between the conjugate and the antibody.

Synthesis of Aflatoxin $B_1$-BSA Conjugate

The synthesis of aflatoxin $B_1$ - BSA conjugate was carried out as follows.

Aflatoxins are water-insoluble, polyheterocyclic, secondary fungal metabolites which have been shown to be mycotoxins. They are produced by *Aspergillus flavus* and *A. parasiticus*, and occur naturally in, e.g., peanuts, peanut meal, cottonseed meal, corn, and dried chili peppers. Types of aflatoxins include aflatoxins $B_1$, $B_2$, $G_1$, $G_2$, $M_1$ and $M_2$, (milk toxins), $B_{2a}$, and $G_{2a}$. Aflatoxins are carcinogenic and extremely toxic.

Aflatoxin $B_1$ was reacted with carboxymethylamine-HCl according to the method of Chu et al. (1977, J. of the AOAC 60: 791) and coupled to BSA by the method of Chu et al. (1977, App. Env. Micro 33: 1125). Briefly, aflatoxin $B_1$ and carboxymethylamine HCl were refluxed in pyridine-methanol-water (1 : 4 : 1), concentrated, and dried. The dried mixture was redissolved in methanol-chloroform (1 : 9) and eluted from an Adsorbosil-5 column with chloroform and methanol-chloroform. The product, aflatoxin $B_1$-1-(o-carboxymethyl) oxime, was then added to BSA and 1-ethyl-3,3,-dimethylamino propyl-carbodiimide, stirred, and the resulting conjugate purified by dialysis against distilled water. The conjugate was then stored at 2°–7° C. until further use.

Assay for Aflatoxin $B_1$

Antibodies were raised to the aflatoxin $B_1$ - BSA conjugate in rabbits using intradermal innoculation. Complete Freund adjuvant and additional *M.tuberculosis* (20 mg/rabbit) were used to induce the antibody response. Antibodies were then Purified by standard procedure.

The reactivity of the conjugate was compared to fresh Aflatoxin $B_1$ standards, using the above antibody, and a standard curve was created, relating aflatoxin $B_1$ levels to conjugate levels. The conjugate was used as an alternate standard to aflatoxin $B_1$ Since the conjugate is stable, can be stored in aqueous solution, and is not toxic, it provides a simple, reliable assay or control standard for the immunoassay.

Other embodiments are within the following claims.

We claim:

1. A method for measuring a hapten in a sample, said hapten being poorly soluble in aqueous solution, having an aqueous solubility of less than 0.01 g/ml, said method comprising providing a standard of known concentration, said standard comprising a water soluble conjugate of said hapten and a protein which is water soluble and which has a molecular weight greater than 1,000 Daltons;

separately contacting said standard and said sample with an antibody specific for said hapten to form antibody-hapten and antibody-hapten conjugate complexes; and measuring the concentration of said hapten in said sample by directly comprising the result of said standard with the result of said sample.

2. The method of claim 1 wherein said hapten is a mycotoxin, a pesticide, or penicillin.

3. The method of claim 2 wherein said mycotoxin is an aflatoxin.

4. The method of claim 3 wherein said aflatoxin is aflatoxin $B_1$.

5. The method of claim 1 wherein said protein is bovine serum albumin, ferritin, lactalbumin, human serum albumin, or polylysine.

6. The method of claim 1 wherein said hapten is a pesticide.

7. The method of claim 6 wherein said pesticide is DDT.

* * * * *

UNITED STATES PATENT AND TRADEMARK OFFICE
CERTIFICATE OF CORRECTION

PATENT NO. : 5,166,078

DATED : November 24, 1992

INVENTOR(S) : Philip L. McMahon and Susan Faust

It is certified that error appears in the above-identified patent and that said Letters Patent is hereby corrected as shown below:

Column 3, line 13, insert --.-- after "$B_1$".

Signed and Sealed this

Eighteenth Day of October, 1994

Attest:

BRUCE LEHMAN

Attesting Officer

Commissioner of Patents and Trademarks